United States Patent [19]
Malone

[11] Patent Number: 5,341,685
[45] Date of Patent: Aug. 30, 1994

[54] METHOD AND APPARATUS FOR NON-DESTRUCTIVE TESTING OF INNER LEAD TAB BONDS AND SEMICONDUCTOR CHIPS

[75] Inventor: Steven Malone, Orlando, Fla.

[73] Assignee: Martin Marietta Corporation, Bethesda, Md.

[21] Appl. No.: 42,632

[22] Filed: Apr. 5, 1993

[51] Int. Cl.$^5$ ............................................. G01N 3/08
[52] U.S. Cl. ............................................. 73/827
[58] Field of Search ........................ 73/37, 827, 834

[56] References Cited

U.S. PATENT DOCUMENTS

| | | |
|---|---|---|
| 3,559,054 | 1/1971 | Bowers . |
| 3,581,557 | 6/1971 | Drees et al. .................. 73/827 |
| 4,453,414 | 6/1984 | Ronemus et al. .............. 73/827 |
| 4,794,800 | 1/1989 | Atkinson ........................ 73/827 |
| 5,085,084 | 2/1992 | Salatino ......................... 73/827 |
| 5,214,963 | 6/1993 | Widder ........................... 73/827 |

FOREIGN PATENT DOCUMENTS 63-250147 10/1988 Japan .

OTHER PUBLICATIONS

Bernardo et al., "Air-Checking Fixture for Soldered PC Boards," IBM Technical Disclosure Bulletin, vol. 23, No. 9, Feb. 1981, pp. 4074–4075.

*Primary Examiner*—Robert Raevis
*Attorney, Agent, or Firm*—Finnegan, Henderson, Farabow, Garrett & Dunner

[57] ABSTRACT

A method and an apparatus for determining the operability of a semiconductor chip including at least one bond between the semiconductor chip and at least one electrical lead, the at least one electrical lead having a first surface, the at least one bond connecting the first surface to the semiconductor chip. The apparatus has a handling carrier rigidly supporting the semiconductor chip, a test socket containing the handling carrier for providing an electrical path from the test socket to the at least one electrical lead and through the at least one bond to the semiconductor chip and back, and a computer for applying an electrical signal to the electrical path for generating an output signal. A gas nozzle is provided, positionable near the first surface, for directing a gas flow at the first surface while an electrical signal is applied. The gas flow generates a force on the electrical lead in a direction away from the semiconductor chip. The computer compares the output signal with a predetermined, characteristic signal to determine operability of the semiconductor chip.

19 Claims, 4 Drawing Sheets

METHOD AND APPARATUS FOR NON-DESTRUCTIVE TESTING OF INNER LEAD TAB BONDS AND SEMICONDUCTOR CHIPS

BACKGROUND OF THE INVENTION

1. Field of the Invention

The present invention relates to the testing of tab bonds between electrical leads (a.k.a. tabs) and the substrate to which the tabs are attached. The present invention also relates to the testing of semiconductor chip components. Specifically, the present invention relates to a method for the non-destructive testing of the strength of tab bonds by directing a gas at the electrical leads while a current is passed through the electrical leads. During the electrical test of the tab bonds, the semiconductor chip is simultaneously, electrically tested.

2. Description of the Related Art

In the manufacture of semiconductor chips, it is important to assure both the quality and reliability of the chips and their attendant leads. During the manufacture of semiconductor chips, electrical lead wires must be firmly attached to the semiconductor chip so that the chip may be incorporated into still larger components. Usually, the electrical leads are affixed to the semiconductor chip by soldering. Each soldered area, however, presents a potential location where the electrical lead may detach from the semiconductor chip. Wherever the electrical lead disengages from the semiconductor chip, there is an electrical break which renders the semiconductor chip useless.

Traditionally, a visual inspection of the semiconductor chip and electrical leads has been conducted to determine whether the semiconductor chip is properly constructed. During the traditional test, if an inspector found a tab that was either loose or disconnected from the semiconductor chip, the component was rejected from service.

However, the visual inspection method is both slow and unreliable. Although visual inspection may readily detect the absence of electrical leads or tabs, visual inspection is impractical for determining whether tabs are only marginally bonded to the semiconductor chip. In such instances, the inspector may pass a chip with apparently well-constructed bonds, but the bonds may fail later in the manufacturing process because of inadequate tab bond strength. Inadequate bond strength may also lead to failure of the component during use.

Mechanical testing is a known alternative to the visual inspection method. Usually, the mechanical test is accomplished by applying pressure to the electrical lead with a needle or other suitable object. The needle comes into actual physical contact with the electrical lead. However, the mechanical inspection method is as inefficient as the visual inspection technique. Additionally, a mechanical test may destroy bonds which are otherwise acceptable for service because of the physical contact with the electrical leads. Finally, a mechanical test cannot detect marginally bonded electrical leads which may fail during use.

Not only is it necessary to test the strength of the bonds between the electrical leads and the semiconductor chip to assure adequate electrical contact, it is also necessary to test the chip to assure that the semiconductor chip is not itself faulty. To test the semiconductor chip, an electrical current is applied to the chip through the electrical leads. The chip should display a characteristic output signature if it is functioning properly. If defective, the electrical output signal will deviate from the expected, characteristic output signal. As with the case of a defective electrical lead, if a semiconductor chip is defective, it must be rejected from service or repaired and tested again.

The prior art fails to display the individual features which characterize the present invention. For example, U.S. Pat. No. 3,559,054, issued Jan. 26, 1971 to R. W. Bowers, discloses a method for mechanically and electrically testing the quality of joints bonding a chip device to the surface of a substrate of a microminiature module. In effect, a high velocity air blast is directed toward the chip device and the electrical resistance is measured between the chip and its substrate. A faulty bond between the chip and the substrate either will blow the chip off the substrate or will cause a detectable change in resistance between the chip and the substrate. However, this method fails to test either tab bond strength or semiconductor chip operability.

U.S. Pat. No. 3,581,557, issued on Jun. 1, 1971 to J. Drees et al., discloses a pneumatic lead wire tester. The strength of the two bonds between a leadwire, a semiconductor die, and a corresponding semiconductor package lead is tested by passing a gas pulse of selected duration past the leadwire so as to create drag forces on the leadwire. If either bond is defective, the drag forces on the leadwire are sufficient to destroy that bond. The bond then can be reformed or the device can be discarded. The destruction of either bond is detected by visual inspection.

Japanese laid-open patent application 63-250147 of Hiromasa Tsukamoto, laid open on Oct. 18, 1988, discloses yet another method for inspecting the bondability of a wire bond. Tsukamoto teaches that a gas may be directed against the lead wires. If defective, the lead wires will disengage from the substrate. The wires which disengage from the substrate can then be detected visually.

Therefore, in each of the traditional tests for determining the strength of the bonds between the electrical leads and the semiconductor chip, including the examples provided above, the apparatus and/or method fails to provide for simultaneous testing of the semiconductor chip and the tab bonds. The electrical test of the semiconductor chip traditionally has been conducted separately from the test of the electrical leads. Therefore, in each of the prior instances, the electrical test of the semiconductor chip adds a second step to the overall method for approving a semiconductor component for service.

Moreover, each of the prior art methods for testing the bondability of leadwires to their respective substrates fails to provide a method for applying a non-destructive force on the leadwires which directly opposes the bonding force of the tab bonds. In each of the prior art cases, the non-destructive force is merely tangentially applied to the leadwires, as each of the figures in the references depict.

SUMMARY OF THE INVENTION

The present invention overcomes the inadequacies associated with the traditional inspection methods in at least two respects. First, the present apparatus and method offer a mechanized testing procedure for rapid determination of the strength of the bond between each individual electrical lead and the semiconductor chip.

Second, the present invention provides for the simultaneous testing of both the tab bonds and the semiconductor chip. By combining an electrical test of the tab bonds and the semiconductor chip, the inspection method of the present invention provides much greater reliability and reproducibility over the prior art inspection methods. The combined test also reduces the overall time required for quality assurance checks. Finally, because the gas flow of the present invention is oriented in direct opposition to the connecting force provided by the tab bond, an adequate test of the tab bonds is assured.

In accordance with the present invention as embodied and broadly described herein, the apparatus for determining the operability of a semiconductor chip and at least one electrical lead includes a support for the semiconductor chip, otherwise known as a handling carrier, to hold the semiconductor chip rigidly during testing. The handling carrier is mounted in a test socket which is electrically connected to the electrical leads bonded to the semiconductor chip. The test socket, in turn, contains pins 8 extending from its underside which are soldered to a load board. The test socket can be unsoldered and removed from the load board, if necessary. The load board is a circuit board which is attached to a test computer for applying an electrical signal through an electrical path which includes the tab bonds and the semiconductor chip. In testing the chip and the electrical leads, the handling carrier is removably inserted into the test socket. An electrical current is applied from the test computer through the load board to the test socket. From the test socket, the current is passed through the electrical leads, the tab bonds, and the semiconductor chip to produce an output signal from the semiconductor chip.

During the electrical test, a gas nozzle is brought into close proximity with the electrical leads. A gas flow is directed against each of the electrical leads as the gas nozzle is moved around the semiconductor chip. As a result, each electrical lead is tested individually. If a lead is loose, the gas flow will disengage the lead from the semiconductor chip.

As a result, while the electrical leads and the semiconductor chip are under electrical test, one of three outcomes are possible. While each of the electrical leads are tested, if the output signal adequately matches the characteristic signal for the particular semiconductor component, the component will be passed for further manufacturing. If one of the leads is not properly connected to the semiconductor chip during the electrical test, the output from the semiconductor chip will not display the characteristic signal and the chip will be rejected from service. Alternately, if the electrical leads are properly attached to the semiconductor chip, but the electrical output from the semiconductor chip does not match the acceptable output expected from the component, the chip will be rejected.

To overcome the difficulties inherent in the prior art, the present invention provides an apparatus for determining the operability of a semiconductor chip including at least one bond between the semiconductor chip and at least one electrical lead, the at least one electrical lead having a first surface, the at least one bond connecting the first surface to the semiconductor chip. As stated previously, the apparatus has a handling carrier for rigidly supporting the semiconductor chip, a test socket for containing the handling carrier and for providing an electrical path from the test socket to the at least one electrical lead and through the at least one bond to the semiconductor chip and back, means for applying an electrical signal to the electrical path for generating an output signal, a gas nozzle, positionable near the first surface for directing a gas flow at the first surface while an electrical signal is applied to the electrical path, the gas nozzle for generating a force on the electrical lead in a direction away from the semiconductor chip, and means for comparing the output signal with a predetermined, characteristic signal for determining operability of the semiconductor chip.

To further overcome the inadequacies of the prior art, and in accordance with the present invention as broadly described and embodied herein, the present invention provides a method for testing the operability of a semiconductor chip including at least one bond between the semiconductor chip and at least one electrical lead, the at least one electrical lead having a first surface, and the at least one bond connecting the first surface to the semiconductor chip, the test comprising the steps of mounting the semiconductor chip to a support to fixedly hold the semiconductor chip during testing, removably contacting a test lead with the at least one electrical lead defining an electrical path from the test lead through the at least one bond to the semiconductor chip and back, applying an electrical signal through the electrical path generating an output signal, positioning a gas nozzle a predetermined distance from the at least one electrical lead near the first surface, directing a gas flow at the first surface to generate a force on the electrical lead in a direction away from the semiconductor chip, and comparing the output signal with a predetermined, characteristic signal to determine operability of the at least one bond.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings. Whenever possible, the same reference numbers will be used throughout the drawings to refer to the same or like parts.

Figure 2:
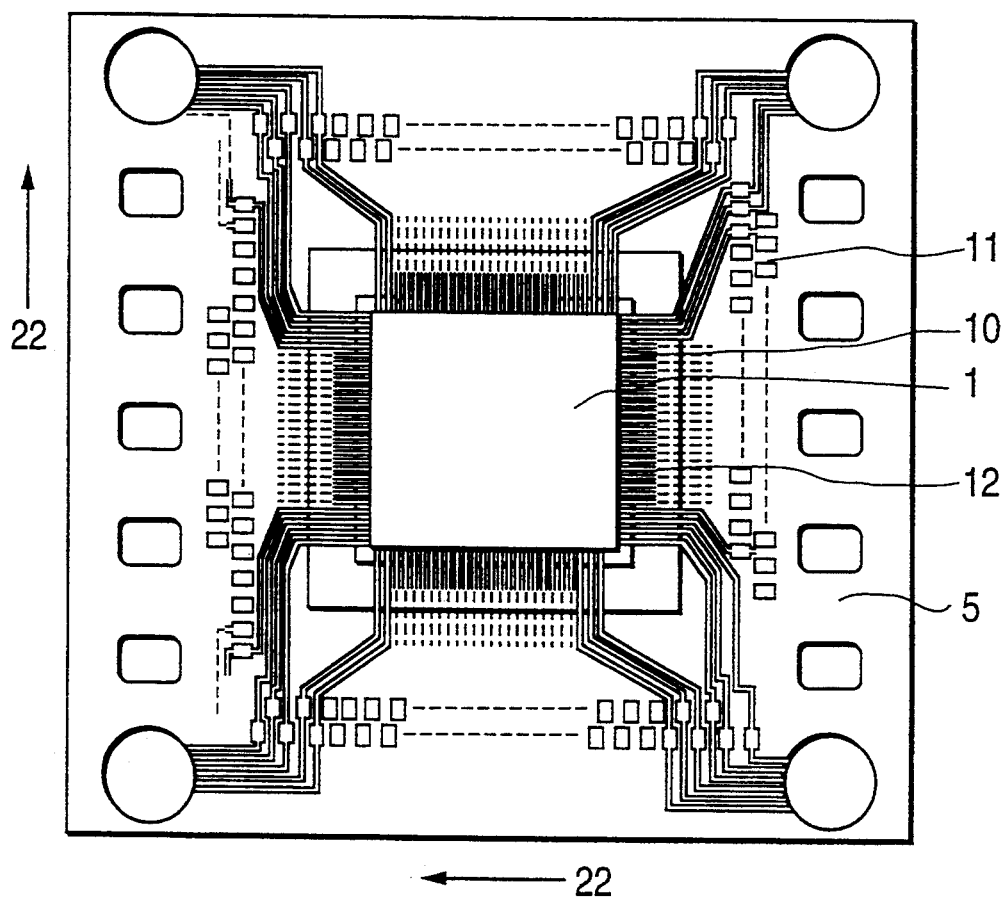
FIG. 2 is a top view illustration of the semiconductor chip with electrical leads.

Referring generally to FIG. 2, the semiconductor chip 1 includes many electrical leads or tabs 12 connected to it. Electrical leads 12 are connected to semiconductor chip 1 by tab bonds 10 which are disposed along the periphery of semiconductor chip 1. First surfaces 15 of electrical leads 12 are connected to semiconductor chip 1 at tab bonds 10. Electrical leads 12 are, therefore, electrically connected to semiconductor chip 1 through tab bonds 10. Tab bonds 10 are disposed along the periphery of semiconductor chip 1 and are typically gold to gold metallurgical bonds formed using, for example, a thermosonic, thermocompression, or soldering process. Electrical leads 12 extend from tab bonds 10 in a direction away from semiconductor chip 1. The free ends of tabs 12 are ultimately, electrically connected to the device in which semiconductor chip 1 is to be incorporated.

Figure 4:
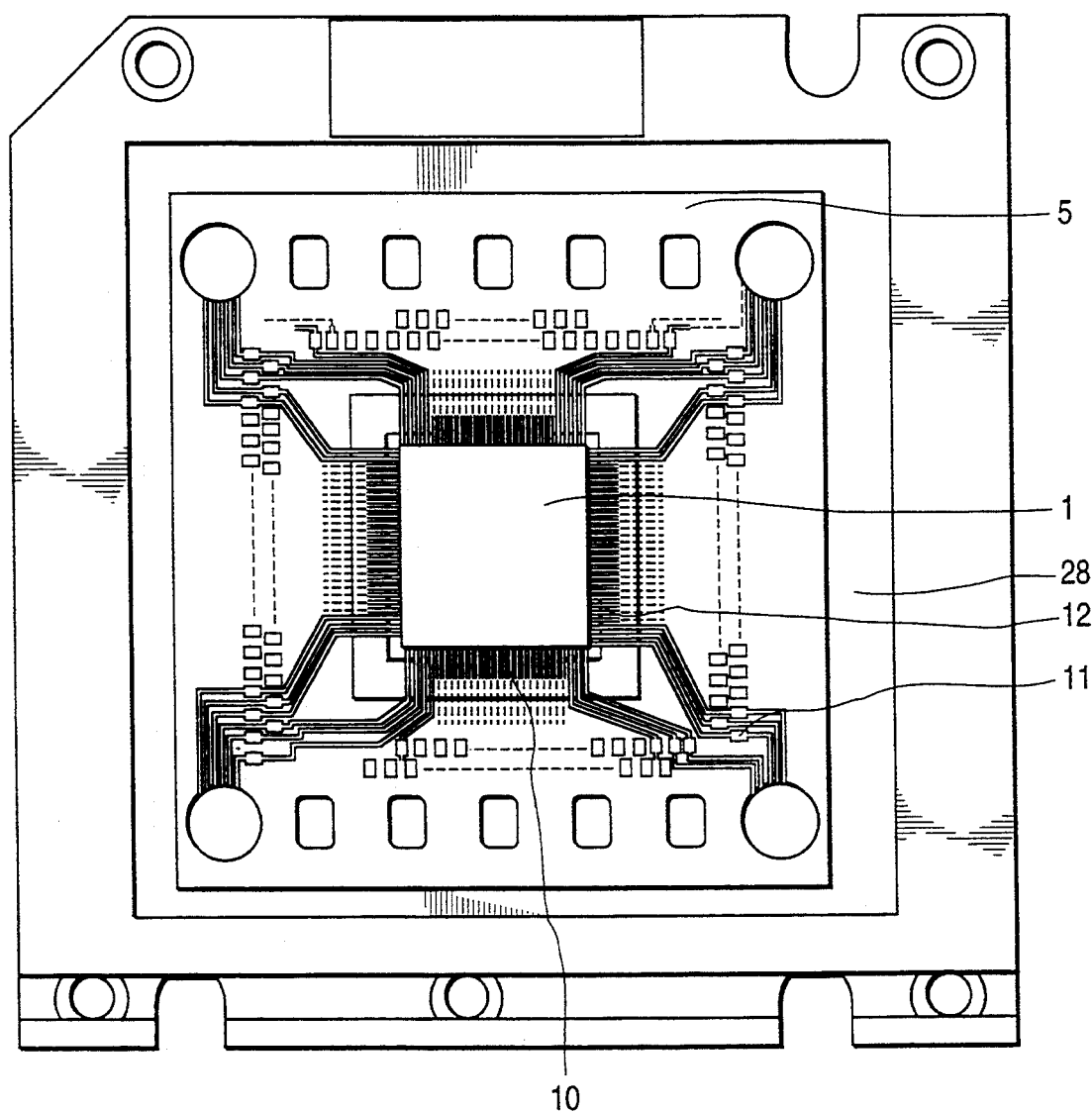
FIG. 4 is a top view illustration of a handling carrier of the present invention containing the lead frame and semiconductor chip.

In accordance with the present invention, the apparatus for determining the operability of a semiconductor chip includes a means for supporting the semiconductor chip during testing. As embodied herein, with reference to FIG. 4, the apparatus includes handling carrier 28 which provides rigid support for semiconductor chip 1 during the electrical test. When gas flow 20 from a gas nozzle such as nozzle 18 is directed at electrical leads 12, as will be described in more detail hereinafter, handling carrier 28 prevents semiconductor chip 1 from becoming dislodged from test socket 26. Handling carrier 28 also assures that semiconductor chip 1 will not be damaged when gas flow 20 is applied to electrical leads 12. While gas flow 20 is directed at electrical leads 12, if semiconductor chip 1 were not firmly secured, semiconductor chip 1 could begin to flutter within test socket 26 and movement within test socket 26 could damage both semiconductor chip 1 and electrical leads 12. To prevent fluttering of semiconductor chip 1, a chip support or stop 16 is provided in test socket 26. Coupled with the rigid support of handling carrier 28, semiconductor chip 1 is adequately secured for testing. Handling carrier 28 and test socket 26 assure that gas flow 20 affects only the individual electrical leads 12 to which gas flow 20 is directed.

In the preferred embodiment of the present invention, handling carrier 28 is a conventional carrier which is commercially available. An example of such a carrier is the 3M/Textool 35 mm Handling Carrier (part #7-0172-10980-200-017-000) which was used in developing the present invention. Handling carrier 28 can be either disposable or reusable. Generally, it is a frame or body which can withstand high temperatures. Handling carrier 28 houses semiconductor chip 1 and lead frame 5. Handling carrier 28 is designed such that lead frame 5 snaps into handling carrier 28 to provide rigid support for lead frame 5 and, therefore, electrical leads 12, during electrical and mechanical testing, as well as throughout the remainder of the assembly process. Commercially available handling carriers 28 are manufactured in a variety of sizes and are constructed to mate with corresponding electrical test sockets 26.

Handling carrier 28 is an open-faced carrier which holds TAB (Tape Automated Bonding) lead frame 5. Lead frame 5 is attached to the semiconductor chip 1. Lead frame 5 consists of a flexible polyimide film containing electrical leads 12 which have been bonded to semiconductor chip 1 by a previous assembly step. Once semiconductor chip 1 has been bonded to electrical leads 12 of lead frame 5, semiconductor chip 1 and lead frame 5 are snapped into handling carrier 28 and will remain in handling carrier 28 throughout the remainder of the test of semiconductor chip 1. Once semiconductor chip 1 has been deemed functional, semiconductor chip 1, along with electrical leads 12, will be singulated from lead frame 5 and handling carrier 28 for placement onto a substrate or for insertion into a higher level assembly.

Figure 1:
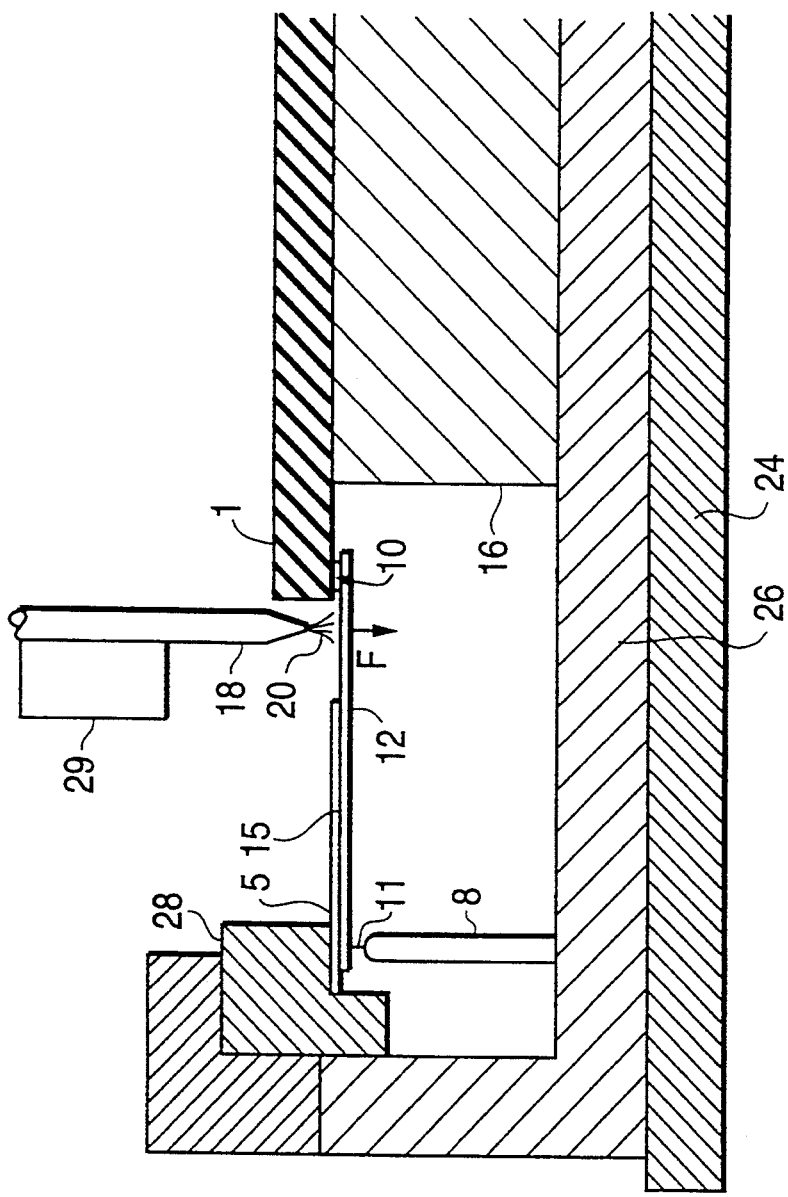
FIG. 1 is a cross-sectional illustration of the apparatus of the present invention taken along line I-I' in FIG. 3.
Figure 3:
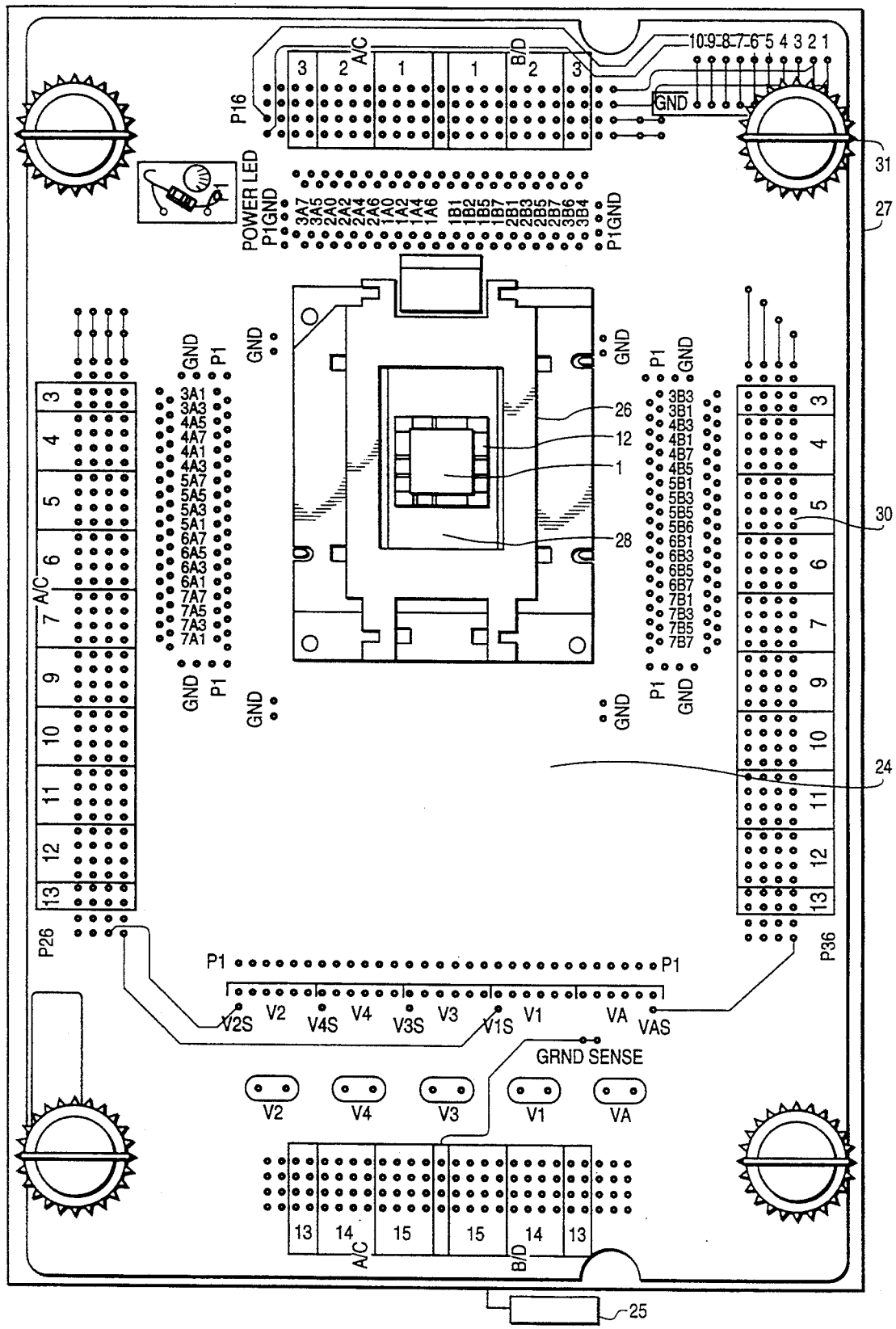
FIG. 3 is a top view illustration of a load board and test socket of the present invention.

Further in accordance with the present invention, a means is provided for containing the handling carrier and for providing an electrical path from the test socket to the at least one electrical lead, through the at least one bond and back. As embodied herein and as illustrated in FIG. 3, the apparatus further includes a test socket 26 for rigidly containing handling carrier 28. Handling carrier 28 is removably insertable into test socket 26. Test socket 26 removably, electrically connects to electrical leads 12 extending outwardly from semiconductor chip 1. Test socket 26 removably connects to electrical leads 12 at the ends disposed away from the periphery of semiconductor chip 1. Test contact point 11 is depicted in FIG. 1. Test contact point 11 is the location where test socket 26 removably connects to electrical leads 12.

Test socket 26 establishes an electrical path through electrical leads 12 to semiconductor chip 1 and back. As will be described in greater detail hereinafter, during the electrical test of semiconductor chip 1, an electrical signal is applied through the electrical path to generate an output signal. The output signal is then compared with a predetermined signal which is characteristic of the particular type of semiconductor chip 1. If the output signal deviates from the predetermined output signature, there is a defect in semiconductor chip 1, and semiconductor chip 1 must be rejected from service. Should semiconductor chip 1 fail the electrical test, semiconductor chip 1 can sometimes be reworked and repaired for retesting. Semiconductor chip 1 need not be discarded in all cases.

In the preferred embodiment of the present invention, test socket 26 is a commercially available conventional device such as the 3M/Textool 35 mm test Socket (part #2-0172-06857-000-125-000) which was used in the development of the present invention. Essentially, test socket 26 is a clamshell-type device which clamps onto electrical leads 12 from semiconductor chip 1.

Test socket 26 is made from a high temperature plastic and contains spring-like pins 8 which make electrical contact with electrical leads 12 extending from semiconductor chip 1 when handling carrier 28 (containing lead frame 5 and semiconductor chip 1) is inserted into test socket 26, and test socket 26 is closed. Test socket 26 includes pins 8 which extend from the bottom of test socket 26 and which are soldered to load board 24 during manufacture. An electrical path is established from the traces running through load board 24, into test socket 26, and to electrical leads 12 extending outwardly from semiconductor chip 1. Currently, there are a number of commercially available test sockets 26 which can accommodate semiconductor chips 1 of various sizes and number of electrical leads 12.

In accordance with the present invention, the apparatus further includes means for applying an electrical signal to the electrical path established from the test socket to the semiconductor chip. As embodied herein, with reference to FIG. 3, computer 25 supplies the electrical signal to semiconductor chip 1 through test socket 26. Computer 25 may be a personal-type computer, if the particular application allows. The electrical signal supplied to semiconductor chip 1 may be a constant electrical signal or it may be a varied signal such as a sine wave. Alternately, the electrical signal may include various types of electrical signals during the test. Finally, each type of semiconductor chip 1 may be supplied with a different type of electrical signal or arrangement of electrical signals.

As embodied herein, computer 25 is an IBM AT Personal Computer linked to an IMS XL-100 Tester, which is the arrangement used for development of the present invention. Test computer 25, otherwise referred to as the test apparatus, consists of electrical tester 27 linked to computer 25. Load board 24 is removably mounted to electrical tester 27. An electrical path, therefore, exists from from computer 25, to tester 27, and then to load board 24. From tester 27, the electrical path continues through load board 24, into test socket 26, to electrical leads 12, and finally to semiconductor chip 1. Electrical tester 27 is capable of metering signals to and from semiconductor chip 1. The signals for the electrical test are generated and analyzed by computer 25. Test vectors are recorded and inputted into computer 25. These test vectors provide the appropriate parameters and test signals which electrical tester 27 must apply to semiconductor chip 1. Computer 25 and electrical tester 27 may be constructed for any of a variety of applications to suit the testing requirements of the semiconductor chip 1. Computer 25 may also control gas pressure and content.

Although an electrical signal is required to test semiconductor chip 1, the electrical signal need not be supplied from computer 25 to test socket 26 directly. In the present invention, it is preferred that load board 24, as depicted in FIG. 3, be provided to direct the electrical signal from computer 25 to test socket 26. Load board 24 is essentially a printed circuit board to which test socket 26 is soldered. The electrical signals generated from computer 25 are supplied through load board 24 to test socket 26 via electrically conductive printed elements 30. As described, the electrical signals proceed from test socket 26 through electrical leads 12 to semiconductor chip 1.

The load board 24 removably electrically connects with electrical tester 27 by thumb screws 31. Each load board 24 may be designed to test a specific type of semiconductor chip 1. Therefore, depending upon the type of semiconductor chip 1 tested, each load board 24 may differ from another of its type. However, at least one type of load board 24 will have the appropriate electrically conductive printed elements 30 to test at least one type of semiconductor component 1.

As described, handling carrier 28 removably engages test socket 26. Therefore, while one semiconductor chip 1 is being tested, another semiconductor component 1 may be inserted into a second handling carrier 28. In this manner, the time required to test each semiconductor chip 1 is minimized, because the operator need not wait to clear each tested semiconductor chip 1 from its handling carrier 28 and replace it with a subsequent, untested semiconductor chip 1. The operator need only replace one handling carrier 28 for another where each contains a separate, individual semiconductor chip 1.

Further in accordance with the present invention, means are provided for directing a gas flow at the electrical leads. As embodied herein, with reference to FIG. 1, gas nozzle 18 is brought into close proximity to one of electrical leads 12 during the test. A gas flow 20 with a predetermined pressure is applied to first surface 15 of electrical lead 12. Gas flow 20 applied to electrical leads 12 may be of any suitable type of gas including air. In particular applications where oxidation or corrosion of electrical leads 12 or tab bonds 10 may be of particular concern, gas flow 20 may include solely an inert gas such as nitrogen or xenon.

First surface 15 of electrical lead 12 is the surface which connects electrical lead 12 to semiconductor chip 1 through tab bond 10. In directing gas flow 20 against a portion of first surface 15 of electrical lead 12 closely adjacent the respective tab bond 10, a force F is generated on electrical lead 12 which tends to push electrical lead 12 in a direction away from semiconductor chip 1. Therefore, if tab bond 10 does not properly connect electrical lead 12 to semiconductor chip 1, tab bond 10 will fail and electrical lead 12 will separate from semiconductor chip 1. Because gas flow 20 is oriented in direct opposition to the connecting force of tab bond 10 between first surface 15 and semiconductor chip 1, an adequate test of tab bonds 10 is assured. If tab bond 10 fails, either the electrical signal or the output signal will be interrupted. If either signal is interrupted, computer 25 will not detect the expected output signal and semiconductor chip 1 will be rejected.

After testing an individual electrical lead 12, if electrical lead 12 withstands force F directed thereat by gas flow 20, gas nozzle 18 is moved to the next electrical lead 12 for similar testing, and the procedure is repeated. In all, gas nozzle 18 will be moved from one electrical lead 12 to the next in gas nozzle travel direction 22 until each of the electrical leads 12 have been thoroughly tested.

During the testing procedure, gas flow 20 may be continuously applied to electrical leads 12 as gas nozzle 18 is moved about the periphery of semiconductor chip 1 in gas nozzle travel direction 22. In other words, gas flow 20 is not stopped as gas nozzle 18 moves from one electrical lead 12 to the next. While gas nozzle 18 moves about the periphery of semiconductor chip 1, it may programmed to stop at each individual electrical lead 12 for a predetermined period of time.

Alternately, gas flow 20 may be directed at each individual electrical lead 12 only when gas nozzle 18 is in close proximity to the respective first surface 15 of the individual electrical lead 12 under test. When gas flow 20 is intermittently applied to each electrical lead 12, gas flow 20 may be applied for a predetermined time period. In comparison with the continuous discharge approach, applying gas flow 20 to each electrical lead 12 in an intermittent fashion conserves the total gas output.

The means for moving gas nozzle 18 about the periphery of semiconductor chip 1 is a standard computer-controlled X-Y motion table. A standard X-Y motion table or scara robot 29 (an arm-like robot) controls the precise movement of gas nozzle 18. Gas nozzle 18 attaches to the standard X-Y motion table or scara robot 29 via an adjustable linkage which assures that gas nozzle 18 is accurately positioned near electrical leads 12 for the test. The standard X-Y motion table or scara robot 29 may be electrically linked to computer 25 to program the exact movement of gas nozzle 18. Accuracy of the motion of gas nozzle 18 is dependent on the size of both electrical leads 12 and semiconductor chip 1 under test. An overall accuracy of plus or minus one thousandths of an inch ($\pm 1/1000$ in.) should be sufficient in most applications. Programmable robotic and motion equipment are readily and commercially available.

Computer 25 may be used to control the movement of gas nozzle 18 about the periphery of semiconductor chip 1. Alternately, a separate computer may be used to move gas nozzle 18. Each type of semiconductor chip 1 may have a different arrangement or spacing of electrical leads 12. Computer 25 may be programmed to compensate for all possible arrangements of electrical leads 12 especially if electrical leads 12 are not evenly spaced about the periphery of semiconductor chip 1.

In accordance with the present invention, the apparatus includes a means for comparing the output signal from the semiconductor component. As embodied herein and as illustrated in FIG. 3, computer 25 also compares the output signal with a predetermined signal which is stored in the memory. Each semiconductor chip 1 has a specific output signal if it is functioning properly. Computer 25 compares the output with the signature which characterizes a properly functioning semiconductor chip 1. If the output signal does not correspond to the characteristic signature, the semiconductor chip 1 must be rejected from service.

In the preferred embodiment, the apparatus which compares the output signal from semiconductor chip 1 is the same device which supplies the electrical signal to semiconductor chip 1. However, the two need not be the same. In the preferred embodiment of the present invention, computer 25, which supplies the electrical signal and compares the output signal with the characteristic signature, is the same computer 25 which directs gas nozzle 18 in is path about the periphery of semiconductor chip 1.

Furthermore, in the preferred embodiment of the present invention, tab bonds 10 are tested simultaneously with semiconductor chip 1. During the electrical test, gas nozzle 18 is brought into close proximity with an individual electrical lead 12. Gas flow 20 is applied to electrical lead 12 in such a fashion as to apply a force F on electrical lead 12 against the connecting force of tab bond 10 and directly away from semiconductor chip 1. If tab bond 10 is not properly constructed, the pressure from gas flow 20 will partially or wholly separate electrical lead 12 from semiconductor chip 1 and the electrical current applied from test contact point 11 will be interrupted. A variation or break in the electrical current indicates a faulty tab bond 10. If semiconductor chip 1 passes both the test applied to it and tab bonds 10, semiconductor chip 1 is removed from test socket 26 and another is inserted for subsequent testing.

Further, in accordance with the present invention, a method for non-destructively determining the operability of a semiconductor chip includes the step of mounting the semiconductor chip to a means for rigidly supporting the semiconductor chip. As described above and as depicted in FIG. 1, handling carrier 28 rigidly supports semiconductor chip 1 while gas flow 20 is applied to electrical leads 12.

In accordance with the present invention, the method includes a next step of establishing an electrical path through the at least one bond to the semiconductor chip. As embodied herein and as described above, test socket 26 removably connects to electrical leads 12 at electrical test point 11. In connecting with electrical leads 12, test socket 26 establishes an electrical path from test socket 26, through electrical leads 12, to tab bonds 10 and finally to semiconductor chip 1.

Further in accordance with the present invention, the method for determining the operability of a semiconductor component includes the step of applying an electrical signal to the electrical path. As embodied herein and as discussed previously, computer 25 applies the electrical signal to the electrical path to generate an output signal from semiconductor chip 1.

Also in accordance with the present invention, the method for determining the operability of a semiconductor chip includes the step of positioning a gas nozzle a predetermined distance from the electrical lead under test, near the first surface of the electrical lead. As embodied herein and as illustrated in FIG. 1, gas nozzle 18 is juxtaposed near first surface 15 on each electrical lead 12.

The method of the present invention further includes the step of directing a gas flow at the first surface to generate a force on the electrical lead in a direction away from the semiconductor chip. As embodied by the present invention, gas flow 20 is directed against first surface 15 to generate force F on electrical lead 12. Force F is directed away from semiconductor chip 1 and tends to push electrical lead 12 away from semiconductor chip 1. If tab bond 10 is not strong enough to withstand force F, tab bond 10 will fail, and semiconductor chip 1 will not be passed for service.

Finally, in accordance with the method of the present invention for determining the operability of a semiconductor component, the method includes a step of comparing the output signal from the semiconductor chip with a predetermined, characteristic signal. As previously described, computer 25 compares the output signal from semiconductor chip 1 with the signal characteristic for that particular type of component. If the output signal adequately correlates with the characteristic signal, semiconductor chip 1 will pass inspection. Otherwise, it will fail inspection.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for determining the operability of a semiconductor chip including at least one bond between the semiconductor chip and at least one electrical lead, the at least one electrical lead having a first surface, the at least one bond connecting the first surface to the semiconductor chip, the apparatus comprising:
   a handling carrier rigidly supporting the semiconductor chip;
   a test socket for containing the handling carrier and for providing an electrical path from the test socket to the at least one electrical lead and through the at least one bond to the semiconductor chip and back;
   means for applying an electrical signal to the electrical path for generating an output signal;
   a gas nozzle, positionable near the first surface for directing a gas flow at the first surface while an electrical signal is applied to the electrical path, the gas nozzle for generating a force on the electrical lead in a direction away from the semiconductor chip; and
   means for comparing the output signal with a predetermined, characteristic signal for determining operability of the semiconductor chip and at least one bond.

2. The apparatus of claim 1, further comprising:
   a load board electrically connecting the comparing means to the test socket.

3. The apparatus of claim 1, wherein:

the gas flow includes air.

4. The apparatus of claim 1, wherein:
the at least one electrical lead includes a plurality of electrical leads.

5. The apparatus of claim 4, further comprising:
means for sequentially positioning the gas nozzle from one of the plurality of electrical leads to the next.

6. The apparatus of claim 1, wherein:
the gas flow is continuous.

7. The apparatus of claim 1, further comprising:
means operatively connected to the gas nozzle for directing the gas flow at a predetermined flow rate for a predetermined time interval.

8. The apparatus of claim 1, wherein:
the applying means is a computer.

9. The apparatus of claim 1, wherein:
the comparing means is a computer.

10. The apparatus of claim 1, wherein:
the comparing means is included within a computer.

11. A method for testing the operability of a semiconductor chip including at least one bond between the semiconductor chip and at least one electrical lead, the at least one electrical lead having a first surface, and the at least one bond connecting the first surface to the semiconductor chip, the test comprising the steps of:

mounting the semiconductor chip to a support to fixedly hold the semiconductor chip during testing;

establishing an electrical path to the at least one electrical lead and through the at least one bond to the semiconductor chip and back;

applying an electrical signal through the electrical path generating an output signal;

positioning a gas nozzle a predetermined distance from the at least one electrical lead near the first surface;

directing a gas flow at the first surface to generate a force on the electrical lead in a direction away from the semiconductor chip; and comparing the output signal with a predetermined, characteristic signal to determine operability of the semiconductor chip and the at least one bond.

12. The method of claim 11, wherein the at least one electrical lead is a plurality of electrical leads, the method further comprising the step of:
applying the gas pressure successively to each individual electrical lead of the plurality of electrical leads.

13. The method of claim 11, wherein:
the gas flow is directed at the first surface of the at least one electrical lead at a predetermined gas pressure.

14. The method of claim 11, wherein the at least one electrical lead includes a plurality of electrical leads, the method further comprising the step of:
sequentially positioning the gas nozzle from one of the plurality of electrical leads to the next.

15. The method of claim 11, wherein:
the gas flow directed at the first surface is continuous.

16. The method of claim 11, wherein:
the gas flow directed at the first surface is applied at a predetermined flow rate for a predetermined time interval.

17. The method of claim 11, wherein:
a computer applies the electrical signal to the electrical path to generate the output signal.

18. The method of claim 17, wherein:
the computer also compares the output signal with a predetermined, characteristic signal to determine operability of the at least one bond.

19. The method of claim 11, wherein:
a computer compares the output signal with a predetermined, characteristic signal to determine operability of the at least one bond.

* * * * *